(12) United States Patent
Baroni et al.

(10) Patent No.: US 6,509,351 B1
(45) Date of Patent: Jan. 21, 2003

(54) PHENYL- AND PYRIDYL-TETRAHYDRO-PYRIDINES HAVING TNF INHIBITING ACTIVITY

(75) Inventors: Marco Baroni, Vanzago-Milano (IT); Bernard Bourrie, Saint Gely Du Fesc (FR); Rosanna Cardamone, Como (IT); Pierre Casellas, Montpellier (FR); Umberto Guzzi, Vanzago-Milano (IT)

(73) Assignee: Sanofi-Syntelabo, Paris (FR)

( * ) Notice: Subject to any disclaimer, the term of this patent is extended or adjusted under 35 U.S.C. 154(b) by 245 days.

(21) Appl. No.: 10/111,045

(22) PCT Filed: Oct. 19, 2000

(86) PCT No.: PCT/FR00/02910

§ 371 (c)(1),
(2), (4) Date: Apr. 19, 2002

(87) PCT Pub. No.: WO01/29026

PCT Pub. Date: Apr. 26, 2001

(30) Foreign Application Priority Data

Oct. 22, 1999 (FR) .............................................. 99 13206
Jun. 28, 2000 (FR) .............................................. 00 08328

(51) Int. Cl.$^7$ ........................ C07D 401/06; A61K 31/47
(52) U.S. Cl. ........................ 514/307; 514/314; 546/148; 546/149; 546/152; 546/174
(58) Field of Search ................................ 514/307, 314; 546/148, 149, 152, 174

(56) References Cited

U.S. PATENT DOCUMENTS

| | | | |
|---|---|---|---|
| 3,991,061 A | 11/1976 | Chorvat et al. | 514/314 |
| 4,704,390 A | * 11/1987 | Caprathe et al. | 514/230.5 |
| 5,118,691 A | 6/1992 | Jaen et al. | 514/314 |
| 5,776,939 A | 7/1998 | Kroin et al. | 514/255 |

OTHER PUBLICATIONS

Chemical Abstracts No. XP–002142809; Bourrie, Bernard et al; "The neuroprotective agent SR 57746A abrogates experimental autoimmune encephalomyelitis and impairs associated blood–brain barrier disruption: implications for multiple sclerosis treatment."; 1999.

Lombaert, S.D. et al; "Potent non–peptidic dual inhibitors of endothelin–converting enzyme and neutral endopeptidase 24.11."; vol. 7, No. 8, Apr. 22, 1997, pp. 1059–1064.

* cited by examiner

*Primary Examiner*—Zinna Northington Davis
(74) *Attorney, Agent, or Firm*—Paul E. Dupont; Michael D. Alexander

(57) ABSTRACT

The present invention relates to compounds of formula (I):

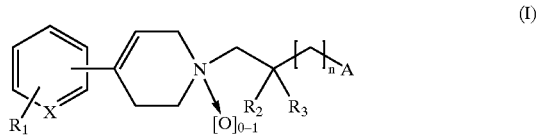

as well as the salts or solvates thereof, to pharmaceutical compositions containing them, to a process for preparing them and to synthetic intermediates in this process.

31 Claims, No Drawings

PHENYL- AND PYRIDYL-TETRAHYDRO-PYRIDINES HAVING TNF INHIBITING ACTIVITY

This application is a 371 of PCT/FR00/02910 filed Oct. 19, 2000.

The present invention relates to novel phenyl- and pyridyl-tetrahydropyridines, to pharmaceutical compositions containing them, to a process for preparing them and to synthetic intermediates in this process.

U.S. Pat. Nos. 5,118,691 and 5,620,988 disclose tetrahydropyridines substituted with a 3-quinolylalkyl radical, which show dopaminergic activity.

It has now been found that certain tetrahydropyridines substituted with a quinolinylalkyl or isoquinolylalkyl radical have powerful activity with respect to modulating TNF-alpha (tumour necrosis factor).

TNF-alpha is a cytokine which has recently aroused interest as a mediator of immunity, of inflammation, of cell proliferation, of fibrosis, etc. This mediator is present in abundance in inflamed synovial tissue and exerts an important role in the pathogenesis of autoimmunity (Annu. Rep. Med. Chem., 1997, 32:241–250).

Thus, according to one of its aspects, the present invention relates to tetrahydropyridines of formula (I):

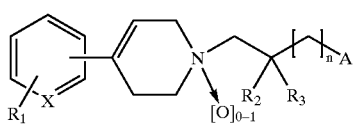

(I)

in which
X represents N or CH;
$R_1$ represents a hydrogen or halogen atom or a $CF_3$ group;
$R_2$ and $R_3$ independently represent a hydrogen atom or a methyl group;
n is 0 or 1;
A represents a group of formula (a) or (b)

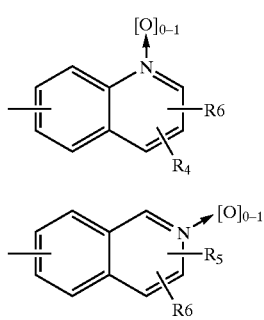

(a)

(b)

in which
$R_4$ represents a hydrogen or halogen atom, a ($C_1$–$C_4$) alkyl group, a $CF_3$ group, an amino group, a mono ($C_1$–$C_4$) alkylamino group or a di ($C_1$–$C_4$) alkylamino group;
$R_5$ represents a hydrogen or halogen atom, a ($C_1$–$C_4$) alkoxy group, a ($C_1$–$C_4$) alkyl group or a $CF_3$ group;
$R_6$ represents a hydrogen atom, a ($C_1$–$C_4$)alkyl group or a ($C_1$–$C_4$)alkoxy group;
as well as the salts or solvates thereof.

In the present description, the term "($C_1$–$C_4$)alkyl" denotes a monovalent radical of a saturated straight-chain or branched-chain $C_1$–$C_4$ hydrocarbon.

In the present description, the term "halogen" denotes an atom chosen from chlorine, bromine, iodine and fluorine.

Preferred compounds are those in which n is zero.

Other preferred compounds are those in which $R_2$ and $R_3$ are hydrogen.

Other preferred compounds are those in which $R_1$ is a $CF_3$ group.

Other preferred compounds are those in which $R_1$ is a fluorine atom.

Other preferred compounds are those in which X is CH and $R_1$ is in position 2 or 3 of the benzene.

Other preferred compounds are those in which X is CH and $R_1$ is a $CF_3$ group.

Other preferred compounds are those in which X is a nitrogen atom and the pyridine is substituted in positions 2 and 6.

According to the present invention, the compounds of formula (I) can exist as N-oxide derivatives. As indicated in the above formula, the compounds of formula (I) can in particular bear the N-oxide group on the tetrahydropyridine or on the quinoline or the isoquinoline of the group A, or alternatively two N-oxide groups may be simultaneously present.

The salts of the compounds of formula (I) according to the present invention comprise both the addition salts with pharmaceutically acceptable inorganic or organic acids such as the hydrochloride, hydrobromide, sulphate, hydrogen sulphate, dihydrogen phosphate, citrate, maleate, tartrate, fumarate, gluconate, methanesulphonate 2-naphthalenesulphonate, etc., and the addition salts which allow a suitable separation or crystallization of the compounds of formula (I), such as the picrate or oxalate, or the addition salts with optically active acids, for example camphorsulphonic acids and mandelic acids or substituted mandelic acids.

The optically pure stereoisomers, and the mixtures of isomers of the compounds of formula (I), due to the asymmetric carbon, when either $R_2$ or $R_3$ is a methyl and the other is a hydrogen, in any proportion, form part of the present invention.

The compounds of formula (I) can be synthesized by a process which involves
(a) reacting the compound of formula (II):

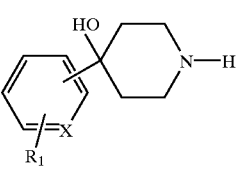

(II)

in which X and $R_1$ are defined as above, with a functional derivative of the acid of formula (III):

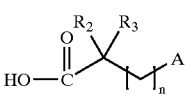

(III)

in which $R_2$, $R_3$, n and A are as defined above,
(b) reducing the carbonyl group of the compound of formula (IV) thus obtained:

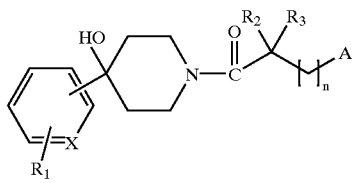

(IV)

(c) dehydrating the intermediate piperidinol of formula (V) thus obtained:

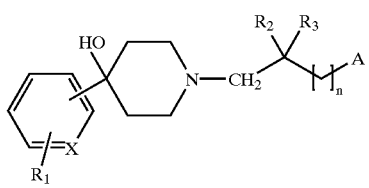

(V)

(d) isolating the compound of formula (I) thus obtained and optionally converting it into a salt or solvate thereof or into the N-oxide derivatives thereof.

The reaction in step (a) can be suitably carried out in an organic solvent at a temperature of between −10° C. and the reflux temperature of the reaction mixture.

It may be preferable to perform the reaction without heating when it is exothermic, such as in the case in which the chloride is used as functional derivative of the acid of formula (III).

Suitable functional derivatives of the acid of formula (III) which can be used are the free acid, optionally activated (for example with BOP=tris(dimethylamino)benzotriazol-1-yloxyphosphonium hexafluorophosphate), an anhydride, a mixed anhydride, an active ester or an acid halide, preferably the bromide. Among the active esters, the one which is particularly preferred is the p-nitrophenyl ester, but the methoxyphenyl, trityl and benzhydryl esters and the like are also suitable.

The reaction solvent preferably used is a halogenated solvent such as methylene chloride, dichloroethane, 1,1,1-trichloroethane, chloroform and the like, but other organic solvents that are compatible with the reagents used, for example dioxane, tetrahydrofuran or a hydrocarbon such as hexane, can also be used.

The reaction may be carried out conveniently in the presence of a proton acceptor, for example an alkaline carbonate or a tertiary amine such as triethylamine.

The reduction in step (b) can be carried out conveniently using suitable reducing agents such as borane complexes, for example dimethyl sulphide/borane ($[CH_3]_2S$—$BH_3$), aluminium hydrides or a lithium aluminium hydride complex in an inert organic solvent at a temperature of between 0° C. and the reflux temperature of the reaction mixture, according to the usual techniques.

The expression "inert organic solvent" means a solvent which does not interfere with the reaction. Such solvents are, for example, ethers, such as diethyl ether, tetrahydrofuran (THF), dioxane or 1,2-dimethoxyethane.

According to one preferred procedure, the process is performed with the dimethyl sulphide/borane used in excess relative to the starting compound (II), at the reflux temperature, optionally under inert atmosphere. The reduction is normally complete after a few hours.

The dehydration in step (c) is readily carried out, for example, using an acetic acid/sulphuric acid mixture, at a temperature of between room temperature and the reflux temperature of the solvent used.

According to a preferred method, the reaction in step (c) is carried out in an acetic acid/sulphuric acid mixture in a ratio of 3/1 by volume, by heating to a temperature of about 100° C. for 1–3 hours.

The desired compound is isolated according to the conventional techniques in the form of free base or a salt thereof. The free base can be converted into one of its salts by simple salification in an organic solvent such as an alcohol, preferably ethanol or isopropanol, an ether such as 1,2-dimethoxyethane, ethyl acetate, acetone or a hydrocarbon such as hexane.

The compound of formula (I) obtained is isolated according to the usual techniques and optionally converted into a salt or solvate thereof or into the N-oxide derivatives thereof.

The compounds of formula (I) can also be prepared by a coupling/reduction reaction starting with a compound of formula (VI):

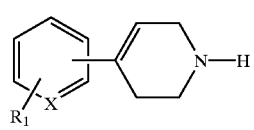

(VI)

in which X and $R_1$ are as defined above, with an aldehyde of formula (VII):

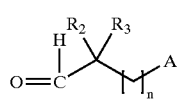

(VII)

in which $R_2$, $R_3$, n and A are as defined above, isolation of the compound of formula (I) and optional conversion into a salt or solvate thereof or into the N-oxide derivatives thereof.

The coupling/reduction reaction is carried out by mixing the starting compounds (VI) and (VII) in an organic solvent such as an alcohol such as for example, methanol, in acidic medium, in the presence of a reducing agent such as sodium cyanoborohydride, according to the conventional methods.

The starting compounds of formulae (II), (III) and (VI) are known or else can be prepared in an analogous manner to that of the known compounds. Such products are described, for example, in WO 97/01536; J. Am. Chem. Soc., 1948, 70:2843–2847; J. Med. Chem., 1997, 40 (7):1049.

The compounds of formulae (IV), (V) and (VII) are novel compounds and constitute a further aspect of the present invention.

The compounds of formula (VII) can be prepared by heating the trifluoromethylsulphonyl derivative (also known as "triflate") of a suitable hydroxy (iso)quinoline with N,N-dialkylethanolamine vinyl ether in the presence of a palladium catalyst and a strong base such as, for example, triethylamine, and by reacting the intermediate thus obtained with concentrated sulphuric acid, according to the usual procedures. Examples of such a process are reported in the experimental section. Alternatively, the compounds of formula (VII) can be prepared by reducing the corresponding acids of formula (III) according to the well-known methods.

The compounds of formula (I) bearing an N-oxide group on the nitrogen atom of the quinoline or of the isoquinoline can be prepared from the N-oxide derivatives of the compounds of formula (III) or (VII). Examples of such syntheses are given in the experimental section.

The compounds of formula (I) bearing an N-oxide group on the nitrogen atom of the tetrahydropyridine can be prepared by oxidation of the corresponding compounds of formula (I). In this case, the compound of formula (I) as obtained by the above syntheses is subjected to an oxidation reaction according to the conventional methods, for example to a reaction with m-chloroperbenzoic acid in a suitable solvent, and isolated according to the usual techniques that are well known to those skilled in the art.

The compounds of the invention have advantageous properties with respect to the inhibition of TNF-$\alpha$.

These properties were demonstrated with the aid of a test aimed at measuring the effect of molecules on the synthesis of TNF-$\alpha$ induced in Balb/c mice by lipopolysaccharide (LPS) from *Escherichia Coli* (055:B5, Sigma, St. Louis, Mo.).

The test products are administered orally to groups of 5 female 7- to 8-week old Balb/c mice (Charles River, France). One hour later, the LPS is administered intravenously (10 $\mu$g/mouse). The blood of each animal is taken 1.5 hours after the administration of the LPS. The samples are centrifuged and the plasma is recovered and frozen at $-80°$ C. The TNF-$\alpha$ is measured using commercial kits (R and D, Abingdon, UK).

In this test, representative compounds of the invention were found to be very active, by inhibiting the synthesis of TNF-$\alpha$ even at very low doses.

By virtue of this activity and their low toxicity, the compounds of formula (I) and the salts or solvates thereof can be used in the treatment of diseases associated with immune and inflammatory disorders or as analgesics. In particular, the compounds of formula (I) can be used for treating atherosclerosis, autoimmune diseases, diseases entailing demyelinization of the neurons (such as multiple sclerosis), asthma, rheumatoid arthritis, fibrotic diseases, pulmonary idiopathic fibrosis, cystic fibrosis, glumerulonephritis, rheumatoid spondylitis, osteoarthritis, gout, bone and cartilage resorbtion, osteoporosis, Paget's disease, multiple myeloma, uveoretinitis, septic shock, septicaemia, endotoxic shock, graft-versus-host reaction, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, disseminated lupus erythematosus, haemodynamic shock, ischaemic pathologies (myocardial infarction, myocardial ischaemia, coronary vasospasm, angina pectoris, cardiac insufficiency, heart attack), post-ischaemic reinfusion attacks, malaria, mycobacterial infections, meningitis, leprosy, viral infections (HIV, cytomegalovirus, herpesvirus), opportunistic infections associated with AIDS, tuberculosis, psoriasis, atopic dermatitis and contact dermatitis, diabetes, cachexia, cancer and radiation-mediated damage.

The compounds of formula (I) and the pharmaceutically acceptable salts and solvates thereof are preferably administered orally.

In the pharmaceutical compositions of the present invention for oral use, the active principle can be administered in unit administration forms, as a mixture with conventional pharmaceutical supports, to animals and human beings for the treatment of the abovementioned complaints. The appropriate unit administration forms comprise, for example, tablets, which may be splittable, gel capsules, powders, granules and oral solutions or suspensions.

When a solid composition in the form of tablets is prepared, the main active ingredient is mixed with a pharmaceutical vehicle such as gelatin, starch, lactose, magnesium stearate, talc, gum arabic or the like. The tablets can be coated with sucrose or other suitable materials or alternatively they can be treated such that they have sustained or delayed activity and such that they release a predetermined amount of active principle continuously.

A preparation in the form of gel capsules is obtained by mixing the active ingredient with a diluent and pouring the mixture obtained into soft or hard gel capsules.

A preparation in the form of syrup or elixir can contain the active ingredient together with a sweetener, preferably a calorie-free sweetener, methylparaben and propyl paraben as antiseptic agents, as well as a flavouring and a suitable colorant.

The water-dispersible powders or granules can contain the active ingredient as a mixture with dispersants or wetting agents, or suspending agents, such as polyvinylpyrrolidone, as well as with sweeteners or flavour enhancers.

The active principle can also be formulated in the form of microcapsules, optionally with one or more supports or additives.

In the pharmaceutical compositions according to the present invention, the active principle can also be in the form of an inclusion complex in cyclodextrins, or ethers or esters thereof.

The amount of active principle to be administered depends, as always, on the degree of progress of the disease as well as the age and weight of the patient. Nevertheless, the unit doses generally comprise from 0.001 mg to 100 mg, better still from 0.01 mg to 50 mg and preferably from 0.1 mg to 20 mg, of active principle, advantageously from 0.5 mg to 10 mg.

According to another of its aspects, the present invention relates to a combination comprising a compound of formula (I) or a pharmaceutically acceptable salt or solvate thereof, and at least one compound chosen from immunosuppressants, such as interferon beta-1b; adrenocorticotropic hormone; glucocorticoids such as prednisone or methylprednisolone; interleukin-1 inhibitors.

More particularly, the invention relates to a combination comprising a compound of formula (I), or a pharmaceutically acceptable salt or solvate thereof, and at least one compound chosen from roquinimex (1,2-dihydro-4-hydroxy-N,1-dimethyl-2-oxo-3-quinolinecarboxanilide), myloran (product from the company Autoimmune containing bovine myelin), antegren (monoclonal human antibody from the companies Elan/Athena Neurosciences) and recombinant interferon beta-1b.

Other possible combinations are those consisting of a compound of formula (I), or a pharmaceutically acceptable salt or solvate thereof, and a potassium-channel blocker such as, for example, fampridine (4-aminopyridine).

According to another of its aspects, the invention relates to a method for treating diseases associated with immune and inflammatory disorders as well as in the treatment of pain, in particular atherosclerosis, autoimmune diseases, diseases entailing demyelinization of the neurons (such as multiple sclerosis), asthma, rheumatoid arthritis, fibrotic diseases, pulmonary idiopathic fibrosis, cystic fibrosis, glumerulonephritis, rheumatoid spondylitis, osteoarthritis, gout, bone and cartilage resorbtion, osteoporosis, Paget's disease, multiple myeloma, uveoretinitis, septic shock, septicaemia, endotoxic shock, graft-versus-host reaction, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, disseminated lupus erythematosus, haemodynamic shock, ischaemic pathologies (myocardial infarction, myocardial ischaemia, coronary vasospasm, angina pectoris, cardiac insufficiency, heart attack), post-ischaemic reinfusion attacks, malaria, mycobacterial infections, meningitis, leprosy, viral infections (HIV, cytomegalovirus, herpesvirus), opportunistic infections associated with AIDS, tuberculosis, psoriasis, atopic dermatitis and contact dermatitis, diabetes, cachexia, cancer and radiation-mediated damage, comprising the administration of a compound of formula (I) or a pharmaceutically acceptable salt or solvate thereof, alone or in combination with other active principles.

The examples which follow illustrate the invention.

Preparation 1

7-isoquinolylacetaldehyde 1.5 g (0.0103 mol) of 7-hydroxyisoquinoline and 5.3 ml of pyridine are cooled to 0° C. 1.86 ml of triflic anhydride are added dropwise thereto. The mixture is stirred for 1 hour at 0° C. and then for 2 hours at room temperature. The resulting mixture is poured into a water/ice mixture and extracted with ethyl acetate, the organic phase is dried and the solvent is evaporated off under reduced pressure. The crude product is purified by chromatography on a column of silica gel, eluting with a 7/3 cyclohexane/ethyl acetate mixture. 7-Hydroxyisoquinoline trifluoromethanesulphonate is obtained in the form of an oil. 1.65 g of this product are mixed with 27.5 ml of anhydrous dimethylformamide, 41 mg of palladium acetate, 1.65 ml of anhydrous triethylamine and 1.38 g of N,N-diethylethanolamine vinyl ether, under argon. This mixture is heated at 80° C. for 36 hours. The resulting mixture is poured into a water/ethyl acetate mixture, the two phases are separated, the organic phase is washed with water and dried, and the solvent is evaporated off under reduced pressure. The residue is purified by chromatography on a column of silica gel, eluting with a 9/1 ethyl acetate/methanol mixture. 2-[2-(7-Isoquinolyl (ethenyl)oxy)]-N,N-diethyl-1-ethanamine is obtained. 1.5 g of this product are treated with 130 ml of water and 13 ml of 96% sulphuric acid. This mixture is heated for 4.5 hours at 60° C. and poured into ice, saturated aqueous NaHCO$_3$ solution is added thereto and the mixture is extracted with ethyl acetate. The organic phase is dried and the solvent is evaporated off under reduced pressure. The title compound is obtained.

Preparation 2

6-Isoquinolylacetaldehyde

Working as described in Preparation 1, but using 6-hydroxyisoquinoline, the title compound is obtained.

Preparation 3

7-Isoquinolylacetaldehyde N-oxide 14 ml of water, 3.5 ml of 96% sulphuric acid and 400 mg of 2-[2-(7-isoquinolyl(ethenyl)oxy)]-N,N-diethyl-1-ethamine obtained as the intermediate product in Preparation 1 are mixed together. 24 ml of methanol are added thereto and this mixture is heated for 5.5 hours at 65° C. The resulting mixture is poured into ice, saturated aqueous NaHCO$_3$ solution is added thereto and the mixture is extracted with ethyl acetate. The organic phase is dried and the solvent is evaporated off under reduced pressure. The product is purified by chromatography on a column of silica gel, eluting with a 1/1 cyclohexane/ethyl acetate mixture to give 7-(2,2-dimethoxyethyl)isoquinoline. 100 mg of this product are dissolved in 15 ml of methylene chloride and 135 mg of m-chloroperbenzoic acid (MCPBA) are added thereto, followed by stirring for 3 hours at room temperature. The mixture is diluted with methylene chloride, aqueous sodium bicarbonate solution is added to neutral pH, the resulting mixture is extracted with methylene chloride, the organic extracts are dried over sodium sulphate and filtered, and the solvent is evaporated off under reduced pressure to give 7-(2,2-dimethoxyethyl)-isoquinoline N-oxide. 105 mg of this product are dissolved in 0.2 ml of methylene chloride and 0.4 ml of a 1/1 trifluoroacetic acid/water mixture is added thereto at a temperature of 0° C. The mixture is stirred at 0° C. for 2 hours and then at room temperature overnight. Methylene chloride is added, the mixture is washed with sodium bicarbonate solution to slightly basic pH, the organic phase is dried over sodium sulphate and filtered, and the solvent is evaporated off under reduced pressure. The title product is obtained.

EXAMPLE 1

6-(2-(4-(3-Trifluoromethylphenyl)-1,2,3,6-tetrahydropyrid-1-yl)ethyl)quinoline and the hydrochloride thereof 1a) 1-(4-hydroxy-4-(3-trifluoromethylphenyl)-1-piperidyl)-2-(6-quinolyl)-1-ethanone A mixture of 2.8 g (0.015 mol) of 6-quinolylacetic acid, 4.2 g (0.0015 mol) of 4-hydroxy-4-(3-trifluoromethylphenyl)piperidine, 6.63 g (0.015 mol) of BOP and 5.3 ml of triethylamine in 60 ml of methylene chloride is stirred overnight. 100 ml of ethyl acetate are added and the mixture is washed with water and with 1N sodium hydroxide solution and dried over sodium sulphate, and the solvent is evaporated off. 5.9 g of the title compound are obtained.

1b) 6-(2-(4-(hydroxy-4-(3-trifluoromethylphenyl)-1-piperidyl)ethyl)quinoline

The product obtained in Example 1a is dissolved in 70 ml of anhydrous THF, it is heated to reflux and 4.05 ml (0.0427 mol) of dimethyl sulphide/borane in 50 ml of THF are added thereto. The mixture is stirred for 15 minutes at room temperature and then for 30 minutes at reflux. The solvent is evaporated off and the residue is taken up in an ethyl acetate/dilute NH$_4$OH mixture, the two phases are separated and the organic phase is washed with water. It is dried over sodium sulphate and the solvent is evaporated off under reduced pressure. The crude product is purified by chromatography on a column of silica gel, eluting with a 9/1 ethyl acetate/methanol mixture. 1.95 g of the title product are obtained.

m.p.=140–142° C.

1c) 6-(2-(4-(3-trifluoromethylphenyl)-1,2,3,6-tetrahydropyrid-1-yl)ethyl)quinoline and the hydrochloride thereof 1.1 g of the product from the above step are dissolved in 12 ml of acetic acid, 3.0 ml of concentrated sulphuric acid are added thereto and the mixture is heated at 100° C. for 2 hours. The resulting mixture is poured into ice, dilute NH$_4$OH is added and this mixture is extracted with ethyl acetate. The organic extracts are washed with water, dried and evaporated under reduced pressure.

The crude product is purified by chromatography, eluting with ethyl acetate. The title compound is obtained. The hydrochloride is prepared using a solution of isopropanol saturated with hydrochloric acid.

m.p. (hydrochloride)=220–222° C.

EXAMPLE 2

7-(2-(4-(3-Trifluoromethylphenyl)-1,2,3,6-tetrahydropyrid-1-yl)ethyl)quinoline and the dihydrochloride dihydrate thereof Working as described in Example 1, but using 7-quinolylacetic acid instead of 6-quinolylacetic acid, the title compounds are obtained.

m.p. (dihydrochloride dihydrate)=216–218° C.

EXAMPLE 3

7-(2-(4-(3-Trifluoromethylphenyl)-1,2,3,6-tetrahydropyrid-1-yl)ethyl)isoquinoline and the dihydrochloride dihydrate thereof 1.75 g (0.0077 mol) of 4-(3-trifluoromethylphenyl)-1,2,3,6-tetrahydropyridine, 30 ml of methanol, 1.15 ml of glacial acetic acid and 0.73 g of anhydrous ethyl acetate are mixed together. The mixture is cooled to 0–5° C. and 1.14 g of 7-isoquinolylacetaldehyde (as obtained from Preparation 1) are added thereto, followed by cautious addition of 1.1 g (0.0175 mol) of sodium cyanoborohydride. The mixture is stirred for 1.5 hours at 0–5° C. and then overnight at room temperature. 7 ml of concentrated hydrochloric acid are added, the resulting mixture is stirred for 10 minutes, the solvent is evaporated off under reduced pressure and the residue is taken up in an ethyl acetate/dilute $NH_4OH$ mixture. The organic phase is dried over sodium sulphate and filtered, and the solvent is evaporated off. The residue is purified on a column of silica gel, eluting with a 9/1 ethyl acetate/methanol mixture. The title compound is obtained. The hydrochloride is prepared using a solution of isopropanol saturated with hydrochloric acid. 1.1 g of product are obtained.

m.p. (dihydrochloride dihydrate)=230–233° C.

EXAMPLE 4

6-(2-(4-(3-Trifluoromethylphenyl)-1,2,3,6-tetrahydropyrid-1-yl)ethyl)isoquinoline and the dihydrochloride dihydrate thereof Working as described in Example 3, but using 6-isoquinolyl acetaldehyde (as obtained from Preparation 2) instead of 7-isoquinolylacetaldehyde, the title compounds are obtained.

m.p. (dihydrochloride dihydrate)=222–224° C.

EXAMPLE 5

6-(2-(4-(3-Fluorophenyl)-1,2,3,6-tetrahydropyrid-1-yl)ethyl)isoquinoline and the dihydrochloride thereof Working as described in Example 3, but using 6-isoquinolyl acetaldehyde (as obtained from Preparation 2) instead of 7-isoquinolylacetaldehyde, and 4-(3-fluorophenyl)-1,2,3,6-tetrahydropyridine instead of 4-(3-trifluoromethylphenyl)-1,2,3,6-tetrahydropyridine, the title compounds are obtained.

m.p. (dihydrochloride)=242–244° C.

EXAMPLE 6

7-(2-(4-(3-Fluorophenyl)-1,2,3,6-tetrahydropyrid-1-yl)ethyl)isoquinoline and the dihydrochloride thereof Working as described in Example 3, but using 4-(3-fluorophenyl)-1,2,3,6-tetrahydropyridine instead of 4-(3-trifluoromethylphenyl)-1,2,3,6-tetrahydropyridine, the title compounds are obtained.

m.p. (dihydrochloride)=227–229° C.

EXAMPLE 7

7-(2-(4-Phenyl-1,2,3,6-tetrahydropyrid-1-yl)ethyl)isoquinoline and the dihydrochloride thereof Working as described in Example 3, but using 4-phenyl-1,2,3,6-tetrahydropyridine instead of 4-(3-trifluoromethylphenyl)-1,2,3,6-tetrahydropyridine, the title compounds are obtained.

m.p. (dihydrochloride)=259–261° C.

EXAMPLE 8

6-(2-(4-(3-Fluorophenyl)-1,2,3,6-tetrahydropyrid-1-yl)ethyl)quinoline and the dihydrochloride thereof Working as described in Example 1, but using 4-hydroxy-4-(3-fluorophenyl)piperidine instead of 4-hydroxy-4-(3-trifluoromethylphenyl)piperidine, the title compounds are obtained.

m.p. (dihydrochloride)=216–218° C.

EXAMPLE 9

7-(2-(4-(3-Trifluoromethylphenyl)-1,2,3,6-tetrahydropyrid-1-oxido-1-yl)ethyl)iso-quinoline and the hydrochloride thereof 0.086 g of m-chloroperbenzoic acid is added, at a temperature of 0–5° C., to a solution of 0.19 g (0.5 mmol) of 7-(2-(4-(3-trifluoromethylphenyl)-1,2,3,6-tetrahydropyrid-1-yl)ethyl)isoquinoline in 25 ml of methylene chloride. The mixture is stirred at 0–5° C. for 2 hours, washed with saturated aqueous sodium bicarbonate solution and the two phases are separated. The organic phase is dried over sodium sulphate, filtered and evaporated under reduced pressure. The product is purified by flash chromatography, eluting with a 1/1 methanol/ethyl acetate mixture to give the title product. The hydrochloride is prepared using a solution of isopropanol saturated with hydrochloric acid.

m.p. (hydrochloride)=166–168° C.

EXAMPLE 10

7-(2-(4-(3-Trifluoromethylphenyl)-1,2,3,6-tetrahydropyrid-1-yl)ethyl)isoquinoline-N-oxide and the hydrochloride thereof Working as described in Example 3, but [lacuna] 7-isoquinolylacetaldehyde N-oxide (as obtained from Preparation 3) instead of 7-isoquinolyl acetaldehyde, the title compounds are obtained.

m.p. (hydrochloride)=198–201° C.

EXAMPLE 11

7-(2-(4-(6-Trifluoromethylpyrid-2-yl)-1,2,3,6-tetrahydropyrid-1-yl)ethyl)isoquinoline and the dihydrochloride dihydrate thereof 0.650 g (0.0028 mol) of 4-(6-trifluoromethyl-2-pyridyl)-1-2,3,6-tetrahydropyridine, 16 ml of methanol, 0.693 g of sodium acetate, 1.6 ml of acetic acid and 1.05 g of 7-isoquinolylacetaldehyde (as obtained from Preparation 1) obtained according to the preparation in 16 ml of methanol are mixed together. This mixture is cooled to 0–5° C. and, after 10 minutes, 1.06 g of sodium cyanoborohydride are added cautiously thereto. The resulting mixture is stirred for 30 minutes at 0–5° C. and then overnight at room temperature. 7 ml of concentrated hydrochloric acid are added, the mixture is stirred for 30 minutes, the solvent is evaporated off under reduced pressure and the residue is taken up in a diethyl ether/dilute $NH_4OH$ mixture to basic pH. The organic phase is dried over sodium sulphate and filtered, and the solvent is evaporated off. The residue is purified by flash chromatography on a column of silica gel, eluting with a 9/1 ethyl acetate/methanol mixture. The title compound (base) is obtained in the form of an oil. The hydrochloride is prepared using a solution of isopropanol saturated with hydrochloric acid. The title compound is obtained in the form of the dihydrochloride dihydrate salt thereof.

m.p. (dihydrochloride dihydrate)=203–206° C.

EXAMPLE 12

6-(2-(4-(6-Trifluoromethylpyrid-2-yl)-1,2,3,6-tetrahydropyrid-1-yl)ethyl)isoquinoline and the dihydrochloride thereof Working as described in Example 11, but using 6-isoquinolylacetaldehyde instead of 7-isoquinolylacetaldehyde, the title compounds are obtained.

m.p. (dihydrochloride)=190–195° C.

EXAMPLE 13

7-(2-(4-(6-Chloropyrid-2-yl)-1,2,3,6-tetrahydropyrid-1-yl)ethyl)isoquinoline and the dihydrochloride thereof Working as described in Example 11, but using 4-(6-chloro-2-pyridyl)-1,2,3,6-tetrahydropyridine instead of 4-(6-trifluoromethyl-2-pyridyl)-1,2,3,6tetrahydropyridine, the title compounds are obtained.

m.p. (dihydrochloride)=110–112° C.

EXAMPLE 14

7-(2-(4-(3-Trifluoromethylphenyl)-1,2,3,6-tetrahydropyrid-1-yl)ethyl)-1,3-dimethylisoquinoline and the dihydrochloride thereof Working as described in Example 3, but using 1,3-dimethyl-7-isoquinolylacetaldehyde, the title compounds are obtained.

m.p. (dihydrochloride)=209° C.

EXAMPLE 15

7-(2-(4-(3-Trifluoromethylphenyl)-1,2,3,6-tetrahydropyrid-1-yl)ethyl)-1,3-diethylisoquinoline and the dihydrochloride thereof Working as described in Example 3, but using 1,3-diethyl-7-isoquinolylacetaldehyde, the title compounds are obtained.

m.p. (dihydrochloride)=192° C.

EXAMPLE 16

7-(2-(4-(4-Trifluoromethylphenyl)-1,2,3,6-tetrahydropyrid-1-yl)ethyl)isoquinoline and the dioxolate thereof Working as described in Example 3, but using 4-(4-trifluoromethylphenyl)-1,2,3,6-tetrahydropyridine instead of 4-(3-trifluoromethylphenyl)-1,2,3,6-tetrahydropyridine, the title compounds are obtained.

m.p. (dioxolate)=138–140° C.

EXAMPLE 17

7-(2-(4-(2-Trifluoromethylphenyl)-1,2,3,6-tetrahydropyrid-1-yl)ethyl)isoguinoline and the dihydrochloride thereof Working as described in Example 3, but using 4-(2-trifluoromethylphenyl)-1,2,3,6-tetrahydropyridine instead of 4-(3-trifluoromethylphenyl)-1,2,3,6-tetrahydropyridine, the title compounds are obtained.

m.p. (dihydrochloride)=158–160° C.

EXAMPLE 18

7-(2-(4-(3-Fluorophenyl)-1,2,3,6-tetrahydropyrid-1-yl)ethyl)quinoline and the hydrochloride thereof Working as described in Example 1, but using 4-(3-fluorophenyl)-1,2,3,6-tetrahydropyridine instead of 4-(3-trifluoromethylphenyl)-1,2,3,6-tetrahydropyridine, and 7-quinolylacetic acid instead of 6-quinolylacetic acid, the title compounds are obtained.

m.p. (hydrochloride)=132° C.

EXAMPLE 19

7-(2-(4-(2-Trifluoromethyl-2-pyridyl)-1,2,3,6-tetrahydropyrid-1-yl)ethyl)quinoline and the dihydrochloride thereof Working as described in Example 3, but using 4-(6-trifluoromethyl-2-pyridyl)-1,2,3,6-tetrahydropyridine instead of 4-(3-trifluoromethylphenyl)-1,2,3,6-tetrahydropyridine, and 7-quinolylacetaldehyde instead of 7-isoquinolylacetaldehyde, the title compounds are obtained.

m.p. (dihydrochloride)=135–136° C.

EXAMPLE 20

7-(2-(4-(2-Trifluoromethyl-2-pyridyl)-1,2,3,6-tetrahydropyrid-1-yl)ethyl)iso-quinoline N-oxide Working as described in Example 3, but using 4-(6-trifluoromethyl-2-pyridyl)-1,2,3,6-tetrahydropyridine instead of 4-(3-trifluoromethylphenyl)-1,2,3,6-tetrahydropyridine, and 7-isoquinolylacetaldehyde N-oxide (as obtained from Preparation 3) instead of 7-isoquinolylacetaldehyde, the title compounds are obtained.

EXAMPLES 21–26

Working as described in the above examples, the following compounds are prepared:

7-(2-(4-(3-trifluoromethylphenyl)-1,2,3,6-tetrahydropyrid-1-yl)ethyl)-3-methylisoquinoline;
7-(2-(4-(3-trifluoromethylphenyl)-1,2,3,6-tetrahydropyrid-1-yl)ethyl)-1-methylisoquinoline;
7-(2-(4-(3-trifluoromethylphenyl)-1,2,3,6-tetrahydropyrid-1-yl)ethyl)-3-ethylisoquinoline. m.p. (dihydrochloride)= 230° C.;
7-(2-(4-(3-trifluoromethylphenyl)-1,2,3,6-tetrahydropyrid-1-yl)ethyl)-1-ethylisoquinoline;
7-(2-(4-(3-trifluoromethylphenyl)-1,2,3,6-tetrahydropyrid-1-yl)ethyl)-3-methoxyisoquinoline;
7-(2-(4-(3-trifluoromethylphenyl)-1,2,3,6-tetrahydropyrid-1-yl)ethyl)-2-methylquinoline. m.p. (dihydrochloride)= 221° C.

What is claimed is:
1. A compound of formula (I):

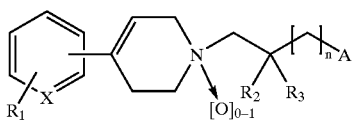

(I)

wherein
X represents N or CH;
$R_1$ represents a hydrogen or halogen atom or a $CF_3$ group;
$R_2$ and $R_3$ independently represent a hydrogen atom or a methyl group;
n is 0 or 1;
A represents a group of formula (a) or (b)

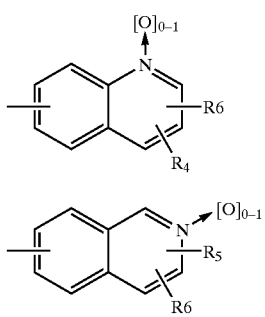

wherein
$R_4$ represents a hydrogen or halogen atom, a $(C_1-C_4)$ alkyl group, a $CF_3$ group, an amino group, a mono $(C_1-C_4)$alkylamino group or a di$(C_1-C_4)$alkylamino group;
$R_5$ represents a hydrogen or halogen atom, a $(C_1-C_4)$ alkoxy group, a $(C_1-C_4)$alkyl group or a $CF_3$ group;
$R_6$ represents a hydrogen atom, a $(C_1-C_4)$alkyl group or a $(C_1-C_4)$alkoxy group; or a salt or solvate thereof.

2. A compound according to claim 1 wherein n is zero.
3. A compound according to claim 1 wherein $R_2$ and $R_3$ are hydrogen.
4. A compound according to claim 1 wherein $R_1$ is a $CF_3$ group.
5. A compound according to claim 1 wherein $R_1$ is a fluorine atom.
6. A compound according to claim 1 wherein X is CH and $R_1$ is in position 3 of the benzene.
7. A compound according to claim 1 wherein X is CH and $R_1$ is in position 2 of the benzene.
8. A compound according to claim 1 wherein X is a nitrogen atom and the pyridine is substituted in positions 2 and 6.
9. A compound according to claim 1 chosen from the mono-N-oxide and bis-N-oxide.
10. A compound according to claim 2 wherein $R_1$ is $CF_3$.
11. A compound according to claim 10 wherein X is CH and $R_1$ is in position 3 of the benzene.
12. A compound according to claim 12 wherein A is a group of formula (b).
13. A compound according to claim 12 wherein $R_5$ and $R_6$ are hydrogen.
14. A compound according to claim 13 selected from the mono-N-oxide and bis-N-oxide.
15. A compound according to claim 13 chosen from 7-(2-(4-(3-trifluormethylphenyl)-1,2,3,6-tetrahydro-1-pyridyl)ethyl)isoquinoline, the mono-N-oxide and bis-N-oxide derivatives thereof and the salts and solvates thereof.
16. A compound of formula (V)

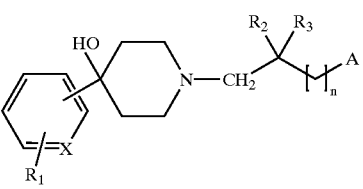

(V)

wherein
X represents N or CH;
$R_1$ represents a hydrogen or halogen atom or a $CF_3$ group;
$R_2$ and $R_3$ independently represent a hydrogen atom or a methyl group;
n is 0 or 1;
A represents a group of formula (a) or (b)

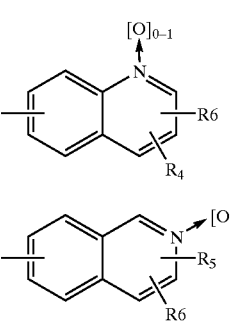

wherein
$R_4$ represents a hydrogen or halogen atom, a $(C_1-C_4)$ alkyl group, a $CF_3$ group, an amino group, a mono $(C_1-C_4)$alkylamino group or a di$(C_1-C_4)$alkylamino group;
$R_5$ represents a hydrogen or halogen atom, a $(C_1-C_4)$ alkoxy group, a $(C_1-C_4)$alkyl group or a $CF_3$ group;
$R_6$ represents a hydrogen atom, a $(C_1-C_4)$alkyl group or a $(C_1-C_4)$alkoxy group;
or a salt or solvate thereof.

17. A compound of formula (IV)

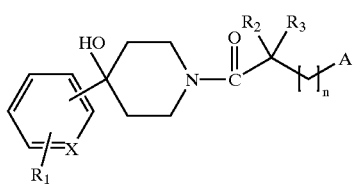

(IV)

wherein

X represents N or CH;

$R_1$ represents a hydrogen or halogen atom or a $CF_3$ group;

$R_2$ and $R_3$ independently represent a hydrogen atom or a methyl group;

n is 0 or 1;

A represents a group of formula (a) or (b)

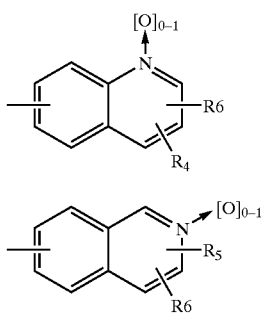

wherein $R_4$ represents a hydrogen or halogen atom, a ($C_1$–$C_4$) alkyl group, a $CF_3$ group, an amino group, a mono ($C_1$–$C_4$)alkylamino group or a di($C_1$–$C_4$)alkylamino group;

$R_5$ represents a hydrogen or halogen atom, a ($C_1$–$C_4$) alkoxy group, a ($C_1$–$C_4$)alkyl group or a $CF_3$ group;

$R_6$ represents a hydrogen atom, a ($C_1$–$C_4$)alkyl group or a ($C_1$–$C_4$)alkoxy group;

or a salt or solvate thereof.

18. A pharmaceutical composition containing, as active principle, a compound according to claim 1.

19. A composition according to claim 18 containing from 0.001 mg to 100 mg of active principle.

20. A pharmaceutical composition containing, as active principle, a compound according to claim 15.

21. A composition according to claim 20 containing from 0.001 mg to 100 mg of active principle.

22. A method of inhibiting TNF-α in a patient in need thereof which comprises administering to said patient an effective amount of a compound according to claim 1.

23. A method of inhibiting TNF-α in a patient in need thereof which comprises administering to said patient an effective amount of a compound according to claim 15.

24. A method for the treatment of inflammation which comprises administering to a patient in need of such treatment an effective amount of a compound according to claim 1.

25. A method for the treatment of inflammation which comprises administering to a patient in need of such treatment an effective amount of a compound according to claim 15.

26. A method of producing analgesics in a patient in need thereof which comprises administering to said patient an effective amount of a compound according to claim 1.

27. A method of producing analgesia in a patient in need thereof which comprises administering to said patient an effective amount of a compound according to claim 15.

28. A method for the treatment of an immune disorder which comprises administering to a patient in need of such treatment an effective amount of a compound according to claim 1.

29. A method for the treatment of an immune disorder which comprises administering to a patient in need of such treatment an effective amount of a compound according to claim 15.

30. A process for preparing a compound of claim 1 wherein a coupling/reduction reaction is carried out on a compound of formula (VI):

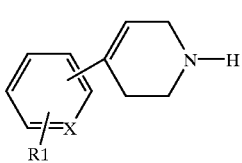

(VI)

wherein X and $R_1$ are as defined in claim 1, with an aldehyde of formula (VII):

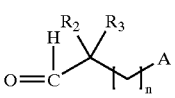

(VII)

wherein $R_2$, $R_3$, n and A are as defined in claim 1.

31. A process for preparing a compound of claim 1 which comprises:

(a) reacting a compound of formula (II):

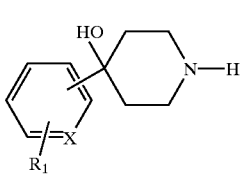

(II)

wherein X and $R_1$ are defined as in claim 1 with a functional derivative of the acid of formula (III):

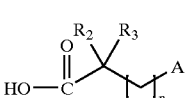

(III)

wherein $R_2$, $R_3$, n and A are as defined in claim 1, (b) reducing the carbonyl group of the compound of formula (IV) thus obtained:

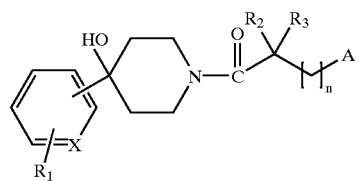
(IV)
and
(c) dehydrating the intermediate piperidinol of formula (V) thus obtained:
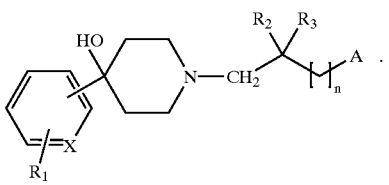
(V)
* * * * *